United States Patent [19]

Masciarotte

[11] Patent Number: 4,967,758
[45] Date of Patent: Nov. 6, 1990

[54] DISPOSABLE COVER/LINER FOR BLOOD PRESSURE MEASURING DEVICES

[75] Inventor: C. Lynn Masciarotte, West Palm Beach, Fla.

[73] Assignee: Prospect Holdings, Inc., Palm Beach, Fla.

[21] Appl. No.: 281,409

[22] Filed: Dec. 8, 1988

[51] Int. Cl.$^5$ .......................... A61B 5/02; B32B 5/26; B32B 5/32; B32B 33/00

[52] U.S. Cl. ..................... 128/686; 428/40; 428/74; 428/76; 428/194; 428/286; 428/302; 428/311.5; 428/311.9; 428/317.3; 428/319.7; 604/372; 604/374; 604/378; 604/385.1; 604/389; 604/390

[58] Field of Search ................ 128/686; 428/40, 74, 428/76, 194, 286, 302, 311.5, 311.9, 317.3, 319.7; 604/372, 374, 385.1, 378, 389, 390

[56] References Cited

U.S. PATENT DOCUMENTS

| | | |
|---|---|---|
| 3,126,297 | 3/1964 | Diamantopoulos et al. |
| 3,310,459 | 3/1967 | Guthrie . |
| 3,316,122 | 4/1967 | Armour . |
| 3,473,525 | 10/1969 | Hanafin ............................ 128/686 |
| 3,658,579 | 4/1972 | Ottinger et al. . |
| 3,881,490 | 5/1975 | Whitehead et al. . |
| 4,047,531 | 9/1977 | Karami . |
| 4,411,660 | 10/1983 | Dawn et al. . |
| 4,609,584 | 9/1986 | Cutler et al. ...................... 428/286 |
| 4,844,965 | 7/1989 | Foxman ............................ 428/286 |
| 4,857,065 | 8/1989 | Seal ................................. 428/913 |

OTHER PUBLICATIONS

Chemicals for Non-Woven Fabrics, J. Taylor, American Dyestuff Reptr., 3/9/59.

*Primary Examiner*—James C. Cannon
*Attorney, Agent, or Firm*—Eckert Seamans Cherin & Mellott

[57] ABSTRACT

A disposable cover or liner for use with all standard cuffs of blood pressure measuring devices (sphygmomanometers). The use of the cover prevents cross contamination between users and hematomas from continuous use of monitoring equipment, protects damaged skin from bacteria on the cuff and prolongs the useful life of the cuff.

The disposable cover/liner is comprised of at least three layers, a first layer of a non-woven web which allows moisture to pass through to a second or middle layer of absorbent material to collect and hold moisture; and the third or outer layer of thin vapor-proof plastic. The cover/liner also has a low-tack adhesive applied to the outer layer in order that the cover/liner can be secured to the inside of the cuff with a peel-off protector.

9 Claims, 1 Drawing Sheet

FIG. 1
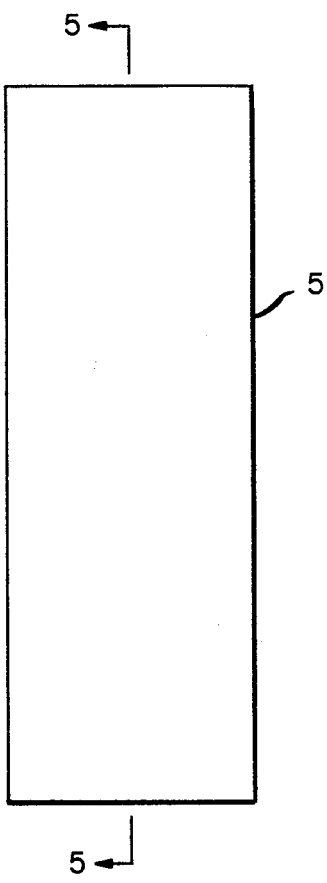
FIG. 2
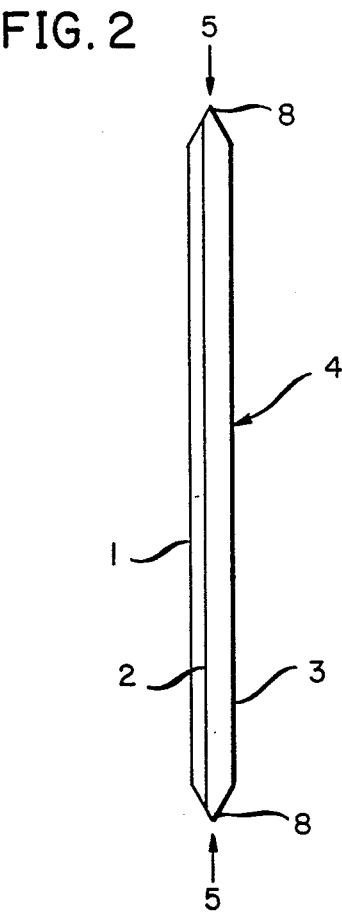
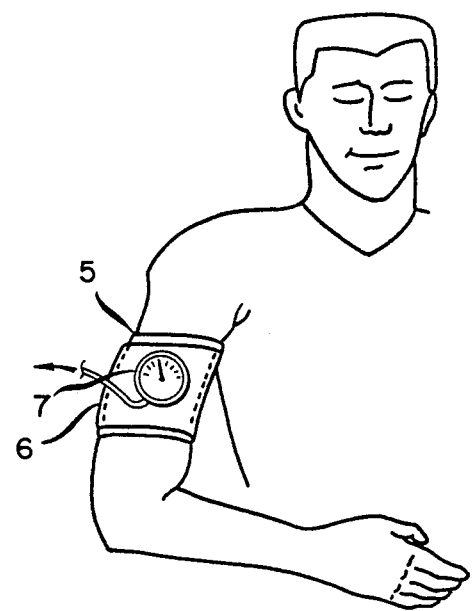
FIG. 3

DISPOSABLE COVER/LINER FOR BLOOD PRESSURE MEASURING DEVICES

BACKGROUND OF THE INVENTION

This invention relates to disposable covers/liners to be used particularly on all standard cuffs currently in use on blood pressure measuring devices, commonly known as sphygmomanometers.

The prior art is devoid of any disposable cuff covers or liners to be used with blood pressure measuring devices. Thus, when a person's blood pressure is taken, the cuffs are placed around the upper arm in contact with the bare skin. The use of the cuff in direct contact with the skin may result in cross contamination between users of the cuff. Further, the continuous use of such monitoring equipment, such as that which occurs in intensive care units, can cause hematomas (blood clots under the skin) and pressure sores. Also, it often becomes wet from the body moisture of the user. Finally, direct contact with the skin causes a build up of moisture and soil on the cuff and decreases the useful working life of the cuff.

The instant invention solves these problems by providing a disposable cuff cover and liner which is inserted inside the cuff before it is placed on the patient's arm or leg to take the patient's blood pressure. The fact that the cover is disposable prevents cross contamination and keeps the cuff from becoming soiled.

The cover/liner is comprised of three layers of material each having a specific purpose. The inner layer consists of a non-woven web which both absorbs moisture from the skin and passes the moisture through the inner layer to the middle layer. The middle layer consists of a moisture absorbent material which collects and holds body moisture from the user. Further, the middle layer, being the thickest of the three layers, provides the padding necessary to prevent hematomas caused by continuous use of the monitoring equipment and the development of pressure sores. Also, both inner layers allow the air to circulate between the cuff and the skin, thereby preventing the possibility of pressure sore development.

The outer layer of the invention is a thin, vapor-proof elastomeric material, which keeps the body moisture from passing through the cover to the cuff and which also has high elasticity to contract and expand with the cuff.

Finally, the cuff cover provides more comfort to the user than when using the cuff by itself, as is currently done when measuring blood pressure.

SUMMARY OF THE INVENTION

In accordance with the foregoing background discussion, this invention provides a cover to fit all standard cuffs in blood pressure measuring devices, which does not affect relative blood pressure readings and which has numerous objects.

One object is to provide a cuff cover which is both disposable and sanitary. A related object of this invention is to provide a cover which prevents cross contamination between users, keeps the cuff from becoming moistured and soiled, and prolongs the useful life of the cuff.

Another object of the invention is to provide a cover of ample thickness and smoothness to help prevent hematomas (blood clots under the skin indicated by black and blue marks).

A further object is to provide a barrier and space between the cuff and the skin, thereby allowing air to circulate, thus preventing the possibility of pressure sore development.

Still a further object of the invention is to provide a cuff cover which is inexpensive, simple to manufacture and easily stored.

The invention accomplishes these and other objects by a cover which is comprised of at least three layers. The first layer which comes into contact with the skin is an absorbent non-woven web, which is smooth textured to assure comfort for the patient and has high strength and flexibility to allow it to expand and contract freely with the cuff. This first layer also has high wicking qualities so that it passes moisture through to the middle layer, which consists of an absorbent material and collects any body moisture. The middle layer is the thickest of the three areas and provides padding to ensure comfort, especially during constant monitoring operations. The third or exterior layer of the cover preferably consists of a thin, vapor-proof synthetic elastomer, which is extremely elastic in order to expand and contract with the expansion and contraction of the cuff during the measuring of blood pressure. Preferably, the outer layer is bonded to the other two layers, thereby creating a cover which is stable in dimension and which resists wrinkles that can cause hematomas on a patient.

Advantageously, the third or exterior face of the outer area, contains an adhesive or holding means, which allows the cover to be affixed to the cuff during its use, and which still can be easily removed afterward.

BRIEF DESCRIPTION OF THE DRAWINGS

FIG. 1 is a front view of the disposable blood pressure device cover;

FIG. 2 is a side cut-away view of the disposable blood pressure device cover along lines 5—5 of FIG. 1; and FIG. 3 is a plan view of the cover in use.

DESCRIPTION OF THE PREFERRED EMBODIMENT

Referring now in detail to the drawings, FIG. 1 shows a front view of the invention and FIG. 2 shows the many layers which make up the invention. The disposable cuff cover 5 consists of at least three layers, the thickness of each layer which may vary. Preferably, the total thickness is not more than approximately 3/32 of an inch in order to allow the cuff to inflate properly and not to alter blood pressure readings.

The inner layer 1 is made of a non-woven web material, smooth in texture to assure patient comfort and at the same time, having sufficient strength and flexibility to expand and contract freely with movement of the cuff. The inner layer 1 should have both absorbing and wicking qualities to pass moisture to the middle layer 2. The inner layer may be formed of paper, a textile structure consisting of a web or mat of fibers held together with a binding material (adhesive). Natural or synthetic fibers and blends thereof may be used, including cotton, rayon, cellulose acetate and triacetate, nylon, acrylic, polyester, paper, wood pulp fibers and the like. Conventional techniques for preparing non-woven fabrics are well known and described in the literature, for example, "Chemicals for Nonwoven Fabrics", J. Taylor, American Dyestuff Reporter, Mar. 9, 1959, and "The New Trend in Fiber Processing Technology", A. J. Bobkowicz, Soil and Crop Science Society of Florida, v. 21, pages 148-170 (1961); R. Krema, "Nonwoven Textiles", Textile Trade Press, Manchester, England (1962); M. McDonald, "Nonwoven Fabrics Technology", Noyes Data Corp., Park Ridge, N.J. (1971); and U.S. Pat. Nos. 3,126,297; 3,316,122; 3,658,579 and 3,310,459, which are herein incorporated by reference.

A major use of non-woven fabrics now being produced commercially is as disposable surgical caps, gowns, pads, drapes and the like for hospital use. Such articles are normally made repellent not only to protect the wearer, but also to prevent the transfer of liquid borne infections from doctor-to-patient-to-doctor.

The middle layer 2 is composed of an absorbent material consisting of a sheet, mat or batting which collects any moisture which is passed through the layer 1. The layer 2 is preferably paper but it can be also comprise a textile material. The middle layer 2 is also thicker than the other layers of the invention to act as padding to ensure patient comfort, especially during constant monitoring operations. The layer 2 may comprise one or more plies of material.

The third and outer layer 3 is preferably a thin, vapor-proof elastomer which is extremely elastic in order to expand and contract with the cuff when blood pressure is taken. The elastomer may comprise natural or synthetic rubbers, or any elastomeric material as described in Modern Plastics Encyclopedia, 1984-85, McGraw-Hill, which is herein incorporated by reference.

The outer layer 3 may be bonded to the other two layers and sealed at both ends 8, thereby creating a unit which is stable in dimension and which resists wrinkles that could cause hematomas on the patient.

Optionally, a holding means may be utilized for holding the cover onto the cuff. The holding means may comprise straps, bands or adhesive means as seen in the drawing. A low-tack adhesive 4 may be placed on the exterior face of the outer layer 3 to allow the cover to be affixed to the invention and yet be easily removed afterward. Further, a peel-off protector could be applied to the adhesive 4 during manufacture and be removed by the user just before the cover is affixed to the cuff. The protector could be a paper or plastic strip.

FIG. 3 shows the invention as it would appear in use. This plan view shows the cover 5 having a width which exceeds slightly the width of the standard cuff 6 of the blood pressure measuring device 7, in order to avoid direct contact between the cuff 6 and skin of the patient.

The advantages of using this disposable cover/liner is conjunction with the cuff when taking blood pressure are numerous. Most important, it prevents cross contamination between patients. Another advantage is that in situations requiring a continuous use of blood pressure monitoring equipment or when using rotating tourniquets, the use of this invention prevents the possibility of hematomas and development of pressure sores because it provides a soft padding between the cuff and the skin and allows air to circulate between the skin and cuff. Furthermore, the use of the cuff in sterile form can protect damaged skin from bacteria on the blood pressure cuff, such as might exist from burns or sores.

In addition to the aforementioned benefits from the use of this invention for the patients, the cover also extends the useful life of the blood pressure cuff by keeping it from becoming moistured and soiled.

In summary, this invention provides a disposable cuff cover/liner for blood pressure measurement devices (sphygmomanometers) which is inexpensive, simple to manufacture and provides numerous benefits to patients.

While the preferred embodiment of the invention and the various modes of utilization have been described in detail hereinabove, it is to be understood that various modifications may be made from specific details described herein without departing from the spirit and scope of the invention.

What is claimed is:

1. A disposable cuff cover or liner for a blood pressure measuring device, which comprises:
   a first layer of non-woven web having high strength and elasticity to allow the cuff to expand and contract freely and high wicking qualities to pass moisture through to a middle layer;
   a middle layer of absorbent material having an absorbent quality to collect moisture which may be passed through the inner layer; and
   a third or outer layer of thin, vapor-proof elastomeric material.

2. The cuff cover according to claim 1 including means for holding said cuff cover onto said blood pressure measuring device.

3. The cuff cover according to claim 3 wherein said holding means comprises adhesive means.

4. The cuff cover according to claim 3 including a protective cover for said adhesive.

5. The cuff means according to claim 1 wherein said first layer comprises paper.

6. The cuff means according to claim 1 wherein said middle layer comprises paper.

7. The cuff means according to claim 1 wherein said third layer comprises a synthetic rubber.

8. The cuff means according to claim 1 wherein said layers are bonded together.

9. The combination of a blood pressure monitoring device having a cuff and the cuff cover of claim 1.

* * * * *